United States Patent [19]

Slaughter

[11] 4,074,110
[45] Feb. 14, 1978

[54] HAND HELD ELECTRIC HEATING DEVICE
[76] Inventor: Philip E. Slaughter, 4552 Elm St., Bellaire, Tex. 77401
[21] Appl. No.: 637,080
[22] Filed: Dec. 2, 1975
[51] Int. Cl.² .................. H05B 1/02; B23K 3/04; H05B 3/06
[52] U.S. Cl. .................. 219/240; 30/140; 32/70; 128/303.1; 219/229; 219/238; 219/501; 219/533; 228/51
[58] Field of Search .................. 219/221–242, 219/533, 501; 228/51–55; 128/303.1, 303.11; 30/140; 200/310, 314; 32/70

[56] References Cited
U.S. PATENT DOCUMENTS

| B 463,388 | 2/1976 | Kraus et al. | 219/233 |
| 748,571 | 1/1904 | Ayer | 219/238 |
| 859,578 | 7/1907 | Perrella | 219/240 UX |
| 2,283,343 | 5/1942 | Weiskopf | 219/227 UX |
| 2,454,576 | 11/1948 | Slack | 219/241 |
| 3,264,449 | 8/1966 | Brenner | 219/227 |
| 3,316,385 | 4/1967 | Anton | 219/236 |
| 3,336,462 | 8/1967 | Fuller | 219/227 |
| 3,466,529 | 9/1969 | Grafham | 219/241 UX |
| 3,766,350 | 10/1973 | Van Dyk et al. | 200/314 |
| 3,883,716 | 5/1975 | Fortune | 219/241 |

FOREIGN PATENT DOCUMENTS

| 917,020 | 9/1946 | France | 219/240 |
| 1,165,176 | 3/1964 | Germany | 219/236 |

Primary Examiner—A. Bartis
Attorney, Agent, or Firm—Pravel, Wilson & Gambrell

[57] ABSTRACT

An electrically powered hand-held heating device having an electrical heating member with a sleeve member disposed thereabout for insulating the user's hand from localized heating of the heating member, a body member formed having an enlarged housing portion and a reduced neck portion. The neck portion releasably engages the heating member and the sleeve member and provides a thermal barrier between the heating member, and the enlarged housing portion while the enlarged housing portion has an electronic control circuit mounted therein for controlling the heating temperature of the heating member for various selected heating ranges.

14 Claims, 17 Drawing Figures

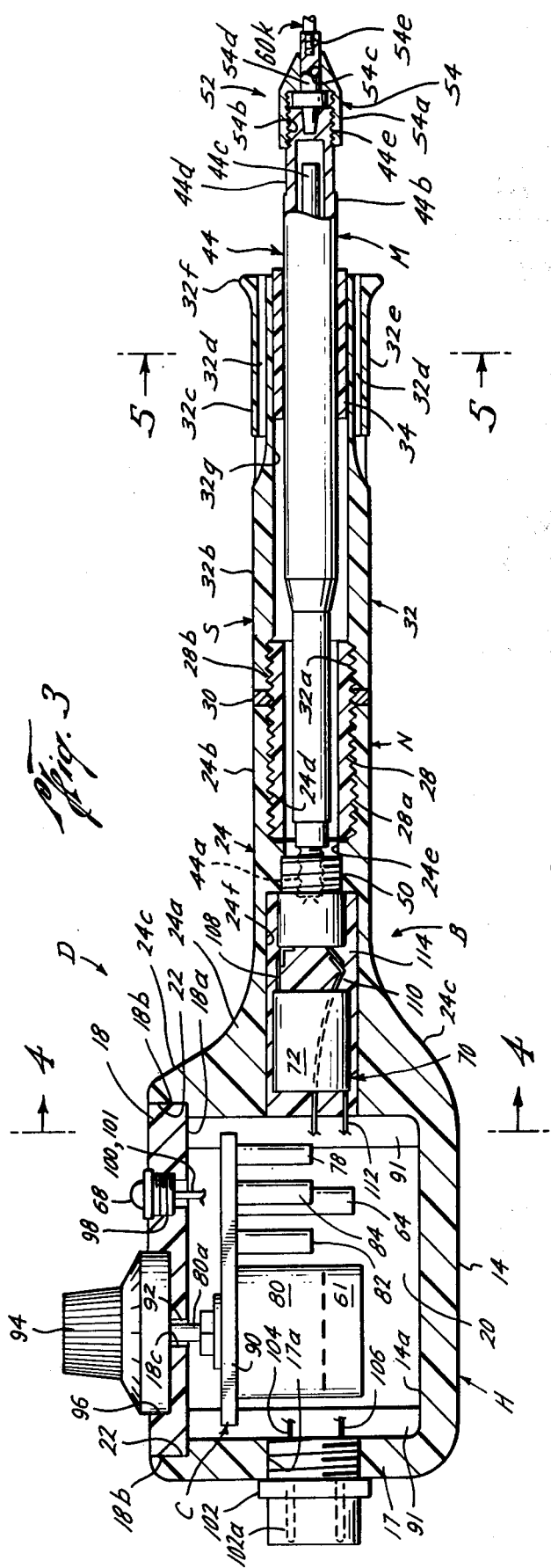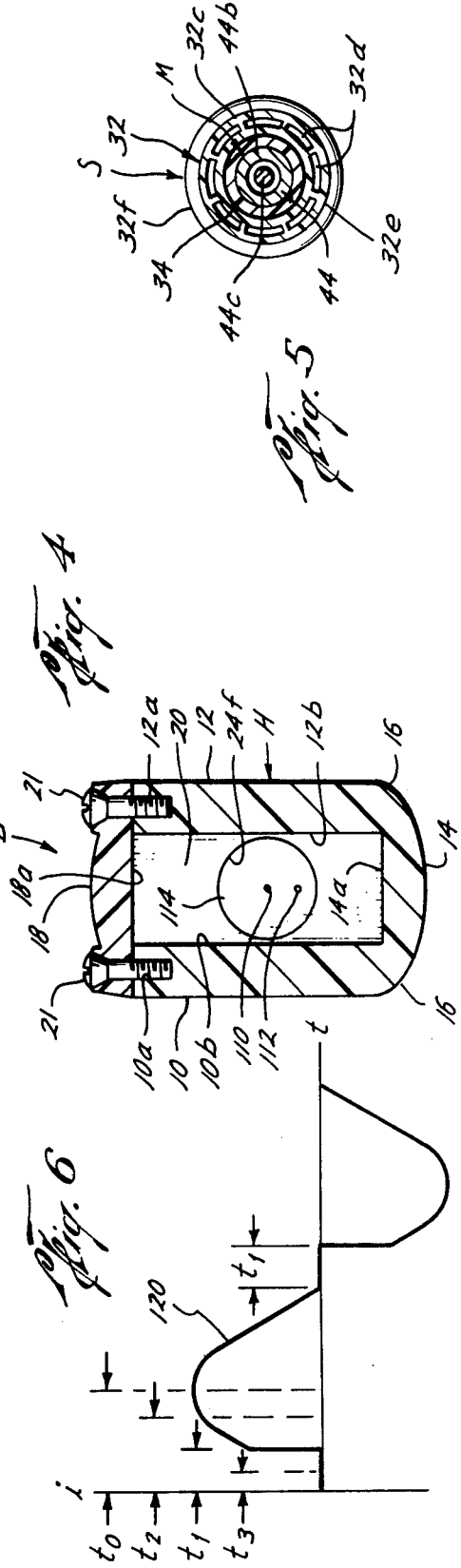

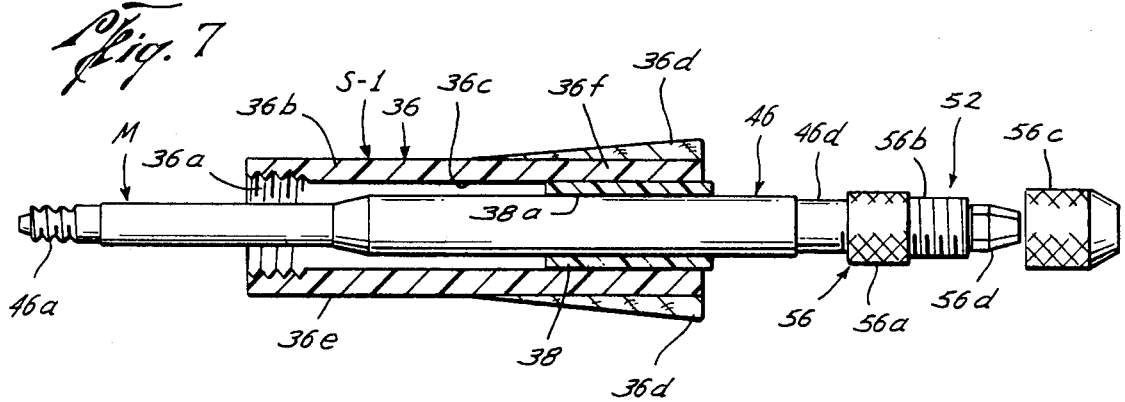
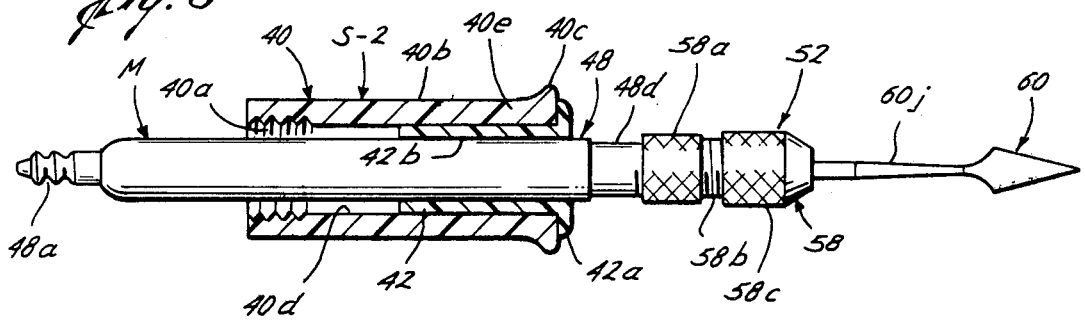
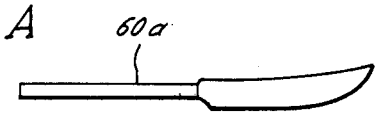 
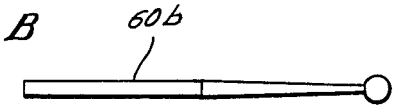 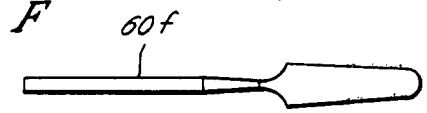
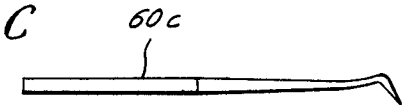 
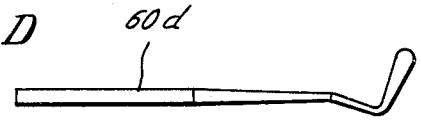 
 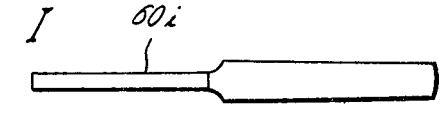

HAND HELD ELECTRIC HEATING DEVICE

BACKGROUND OF THE INVENTION

The field of this invention is heating devices, particularly of the type suitable for jewelry making, electronic assembly and repair, soldering, and the like. Prior art heating devices include those such as disclosed in U.S. Pat. Nos. 3,551,639; 3,662,151; 3,691,342; 3,706,871; 3,716,692; and 3,883,716.

Some of the limitations encountered in these prior art heating devices generally included fixed or limited temperature operation range with no temperature selectivity or adjustment, permanently attached heating elements having one specific temperature range and thus limiting the temperature range of the unit, as well as no provisions for reducing high-frequency electromagnetic radiation typically caused by such heating elements. Still further, most prior art devices failed to provide control switching, such as on off switching and temperature control of the heating units in the hand-held portion of the unit, but rather required additional remote control boxes to contain the control switching with their associated extra electrical wires and the like. With the additional remote control boxes, precise control of temperature was often difficult to obtain, since the user's attention was divided between the tool and the control box. Further, prior art devices, in part, did not provide for proper thermal insulation of heat sensitive electronic components of the network from the heat generated by the heating element resulting in potential damage to such components. Many of such prior art units further did not include a means for indicating that the unit is on or off and/or indicating the amount of heat being generated adjacent the heating tip. Lastly, none of these devices used multiple insulating sleeves for protecting the user's hand from heat generated by the heating tip under varying temperature situations as well as providing for a compact, easily maneuverable, lightweight, well-balanced, hand-held unit.

SUMMARY OF THE INVENTION

The present invention provides a new and improved electrically powered heating device adapted to be held in the hand of a user having electrical heating means for providing localized heating over various selected heating ranges for a variety of applications, sleeve means disposed about the heating means for gripping and thermally insulating the user's hand from the heating means, a body member formed having an enlarged housing portion and a reduced neck portion with the neck portion releasably engaging the heating means and the sleeve means and providing a thermal barrier between the sleeve means and the enlarged housing portion wherein an electronic control circuit for selectively controlling the heating temperature of the heating means over various selected heating ranges is housed.

BRIEF DESCRIPTION OF THE DRAWINGS

FIG. 3 is an elevational view, partially in section, of the heating device of the present invention;

FIG. 4 is a sectional view, taken along the lines 4—4 of FIG. 3, of the heating device of the present invention;

FIG. 5 is a sectional view, taken along the lines 5—5 of FIG. 3, of the heating device of the present invention;

FIG. 6 is a waveform diagram of the current furnished to the heating means by the electronic control circuit of the heating device of the present invention;

FIG. 7 is an elevational view, partially in section, of an alternative heating means and sleeve means of the heating device of the present invention;

FIG. 8 is an elevational view, partially in section, of an alternative heating means and sleeve means for the heating device of the present invention; and, FIGS. 9A through I are elevational views of a number of heating tips to be used with the heating device of the present invention.

DESCRIPTION OF THE PREFERRED EMBODIMENT

Figure 1:
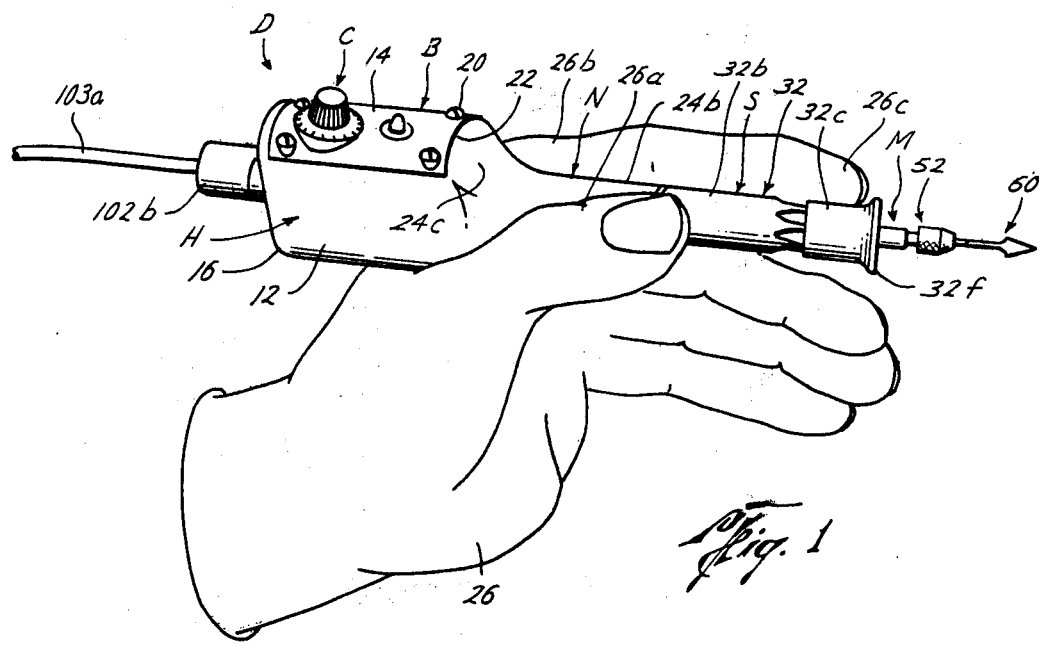
FIG. 1 is an oblique view of the heating device of the present invention as held in the hand of the user.

In the drawings, the letter D designates the heating device of the present invention. The heating device D includes a body member B having an enlarged housing portion H and a neck portion N formed therewith, the neck portion N receiving sleeve means S and electrical heating means M therewith. An electronic control circuit C is mounted within the enlarged housing H.

The heating device D of the present invention includes a body member B formed having an enlarged housing portion H and a neck portion N. Preferably, the body member B is formed of a material that is easily machined, is an electrical insulator, moisture proof, acid proof, wax proof, and will withstand short intervals of time at high heat without charring, burning or becoming excessively hot to the touch. Further, the body member B should be made of a material that is mechanically strong and fairly light in weight and not excessively brittle. For example, a natural linen Bakelite is suitable for meeting such requirements and further is capable of being modified with epoxy cements to facilitate design changes with relative ease. However, other suitable materials may be used if desired.

The enlarged housing portion H may be of any suitable configuration and, as shown in FIGS. 1 and 3, is preferably of a rectangular-cubically shaped configuration, but any other suitable shape may be used. Preferably, the enlarged housing portion H includes side portions 10, 12 (FIG. 4) and curved base portion 14 adjoining such side portions 10, 12 adjacent contoured edges 16. A top portion 18 is removably mounted with the enlarged housing portion H by screws 21, or any other affixing means, that are threadedly received by side portions 10, 12 in threaded openings 10a, 12a, respectively. Interior surfaces 10b, 12b, 14a, 18a of side portions 10, 12, base portion 14, and top portion 18, respectively, define the cavity 20 formed within the enlarged housing portion H. The top portion 18 is preferably adapted to be received in recess 22 (FIGS. 1, 3) formed with the upper portion of the enlarged housing portion H such that end portions 18b (FIG. 3) of the top portion 18 are mounted adjacent such recess 22. The top portion 18 is thus removably mounted with the enlarged housing portion H and engages recess 22 such that the cavity 20 is effectively isolated from adverse environmental effects such as moisture and contact with potentially explosive gases or the like.

The body member B further includes a neck portion N preferably of a tubular configuration, however, any other suitable shape may be used if so desired. Preferably, the neck portion N is of a reduced, cross-sectional area as compared to that of the enlarged housing portion H. The neck portion N includes neck 24 having a first end 24a and a second end 24b. The first end 24a of neck 24 is preferably formed with the enlarged housing portion H by contour surface 24c. Preferably, contour surface 24c conforms substantially to the contour of the portion of the user's hand 26 (FIG. 1) between the thumb 26a and forefinger 26b as discussed more fully hereinbelow. Preferably, the contour surface 24c extends about the circumferential areas adjoining the first end 24a of the neck portion N and the enlarged housing portion H allowing positioning of the heating device D in multiple, comfortable positions in the hand 26 of the user.

The second end 24b of the neck 24 is formed having threads 24d therewith and adapted to receive a threaded coupler 28 by threads 28a compatibly formed therewith. Preferably, the threaded coupler 28 is formed of nylon or any other suitable material having good wear characteristics. Thus, threads 28a of threaded coupler 28 engage threads 24d of neck 24. A sealing coupling ring 30 (FIG. 3), preferably formed of a suitable moisture-resistant, explosion-proof material, such as a synthetic resin polymer, commonly marketed under the name "TEFLON," or any other suitable material is threaded onto threads 28a of threaded coupler 28. The remaining, unthreaded threads 28b threadedly engage the sleeve means S.

The sleeve means S is preferably formed of the same and/or similar materials as used for the body member B as fully described hereinabove, or any other suitable materials may be used. The sleeve means S includes sleeves 32, 36, 40 which may be of a variety of suitable configurations, as shown in FIGS. 3, 7 and 8. As shown in FIG. 3, sleeve 32 is formed having threads 32a adapted to be threaded upon threads 28b of threaded coupler 28. Central tubular portion 32b having threads 32a formed therewith adjacent one end has ventilated portion 32c formed adjacent the other end thereof. The ventilated portion 32c of sleeve 32 has a plurality of longitudinal, ventilation means, such as slotted openings 32d (FIGS. 3, 5) formed therein to allow air flow therethrough such openings as described more fully hereinbelow. The exterior surface 32e of the ventilated portion 32c provides a gripping portion for the user's hand 26 with a lip 32f formed adjacent the end thereof for comfortable positioning of the fingertips 26c adjacent thereto to provide a comfortable resting position for the fingertips 26c of the hand 26 when using the heating device D of the present invention. An insulating bushing 34 is mounted within bore 32g of the ventilated portion 32c of the sleeve 32 and is preferably formed of a synthetic resin polymer, such as that marketed under the name "TEFLON," however, any other suitable material may be used if so desired as long as such material is capable of withstanding high temperatures without any detrimental effects thereto.

As shown in FIG. 7, a sleeve means S-1 includes sleeve 36 adapted to be mounted with the body member B, to be used as an alternative to sleeve 32 depending upon specific heating and/or thermal conditions required. The sleeve 36 includes threads 36a which are adapted to engage threads 28b of threaded coupler 28 for mounting the sleeve 36 therewith neck 24. The sleeve 36 is formed preferably of a tubular body 36b having a bore 36c therethrough. Insulating material 36d, such as cork, or any other suitable material, is appropriately affixed to the exterior surface 36e of the sleeve 36 adjacent end 36f. As with sleeve 32, sleeve 36 has the insulating material 36d formed such that the fingertips 26c of the hand 26 may comfortably engage the same when using such sleeve 36. Insulating bushing 38 is mounted within the bore 36c of the sleeve 36 and has bore 38a adapted to engage the heating means M as described more fully hereinbelow. Preferably, the insulating bushing 38 is formed of a synthetic resin polymer such as that marketed under the name "TEFLON."

As shown in FIG. 8, a sleeve means S-2 includes sleeve 40 which is threadedly mounted with the body member B by threads 40a. The sleeve 40 has a generally tubularshaped body 40b formed with a lip 40c adjacent end 40e thereof for enhancing ease in gripping by the user's hand 26. The sleeve 40 is formed having a bore 40d therethrough which is adapted to receive insulating bushing 42 appropriately formed of a synthetic resin polymer such as that marketed under the name "TEFLON," or any other suitable insulating material. Insulating bushing 42 has lip 42a formed therewith and adapted to engage the exterior end surface of the lip 40c of sleeve 40 with the bore 42B of the insulating bushing 42 engaging the heating means M as more fully described hereinbelow.

Thus, it can be seen that several alternate and interchangeable sleeve means may be used with the heating device D of the present invention by threading the appropriate sleeves 32, 36, or 40 onto the threads 28b of the threaded coupler 28 to position such sleeve with the neck portion N of the body member B for ease in gripping by the user and for thermally insulating the user's hand from the heating means M. Sleeve 36 having insulating material 36d therewith is adapted to be used in high heating situations, while sleeve 32 having ventilated portion 32c is useful for moderate heat applications. Sleeve 40, preferably of shorter overall length than sleeves 32, 36 as discussed more fully hereinbelow, is preferably used for low heating requirements. The bushings 34, 38, 42 act to stabilize the heating means M mounted within the sleeves 32, 36, 40 as well as provide a heat sink for the heat generated by the heating means M without causing excessive heating of the external surfaces of sleeves 32, 36, 40.

The heating device D of the present invention further includes electrical heating means M for providing localized heating over various selected heating ranges for a variety of applications. The heating means M includes heating capsules 44 (FIG. 3), 46 (FIG. 7), and 48 (FIG. 8). The heating capsules 44, 46, 48 are generally of small diameters and of relative short lengths and have high heat capabilities for relatively long intervals of time. Furthermore, preferably the heating capsules 44, 46, 48 should have low current drag and provide for ease in affixing such heating means M with the heating device D of the present invention. For example, those heating capsules marketed under the name "Princess #6918-18 Watt Heat Capsule" by Unger may be used, however, any other suitable heating capsule may be used if so desired. The heating capsules 44, 46, 48 are adapted to be releasably mounted in socket 50 mounted within the bore 24e of the neck 24 by means of threads 44a, 46a, 48a, respectively.

The heating means M may be of any type of insulated resistance element that is electrically insulated from its enclosing external sheath, and if it is of the wound resistance wire-type, should be insulated from each turn of the windings. Alternatively, button or nodule-type resistance elements need only be insulated electrically from the enclosing sheath of such heating elements. Typically, the exterior sheath such as sheath 44b, 46b, 48b, respectively, are formed of some non-brittle metal such that the heating capsules 44, 46, 48 may withstand user abuse without breakage thereof. Preferably, such heating capsules 44, 46, 48 should be hermetically sealed to avoid internal contamination and help prevent the shorting of the heating elements, such as element 44c (FIGS. 3, 5) therewithin sheath 44b. Furthermore, hermetic sealing helps to prevent explosions caused by shorting circuitry and/or the hot, heating element 44c potentially igniting an explosive atmosphere, such as aromatic type gases such as gasoline, ether, chloroform or the like.

The threads 44a, 46a, 48a of heating capsules 44, 46, 48 supply quick-acting connectors to connect the heating means M with the electrical energy source as described more fully hereinbelow. This screw-type connection or alternatively a bayonet locking connection (not shown) provides a safe, positive electrical connection therebetween the heating means M and the electronic control circuit C.

The heating means M further includes collet means 52 mounted with the heating capsules 44, 46, 48 adjacent ends 44d, 46d, 48d, respectively. The collet means 52 as shown in FIGS. 3, 7, 8 include collets 54, 56, 58, respectively, and are adapted to receive heating blades or tips 60 (FIG. 9). The heating blades or tips 60 may be of a variety of configurations as shown in FIG. 9, tips 60a–60i and in FIG. 8, tip 60j. All of such tips 60 are interchangeable and adapted to be positioned in the collet means 52 such that the tips may rotate a full 360° within the collet means 52 allowing full flexibility of positions of the blades or tips 60 with respect to the heating capsules 44, 46, 48. Further, it is important that in addition to the interchangeability feature of the blades or tips 60, that the collet means 52 firmly and positively hold the shank portions of such blades 60 to facilitate and optimize heat transfer from the heat capsules 44, 46, 48 to such blades 60.

Collet 54 includes preferably a knurled cap 54a having threads 54b adapted to engage similar threads 44e formed with heating capsule 44. The cap 54a further includes an opening 54c formed adjacent a generally truncated conically shaped end and adapted to receive insert 54d therewith to securely mount such insert 54d with the heating capsule 44 adjacent the heating end thereof. The insert 54d preferably formed of copper or any other high thermal conductivity material, further includes internal threads 54e adapted to engage heating tips having a threaded shank (not shown) to be removably mounted therewith. Once the threaded tips are secured with the insert 54d, by mere loosening of cap 54a, the tip may be rotated to any desired position and appropriately locked by threading the cap 54a firmly to the threads 44e of the heating capsule 44.

Alternatively, as shown in FIG. 7, the collet means 52 may include collet 56 having an adaptor sleeve 56a adapted to be threaded with the threaded nose of the heat capsule 46 adjacent end 46d with such sleeve 56a having threads 56b therewith and adapted to engage nose portion 56c having threads (not shown) compatible with threads 56b. The nose portion 56c in conventional fashion, has an internal taper cut and adapted to engage collet fingers 56d which circumferentially engage an appropriate blade or tip 60. By inserting the tip 60 therethrough nose portion 56c and thereinto collet fingers 56d with the nose portion 56c thereafter being threaded onto threads 56b, the tip 60 may be securely fastened to the heating capsule 46 in any desired rotated position without the requirement of such tips having a special, threaded end portion to be received thereby such collet 56.

As shown in FIG. 8, collet means 52 further includes collet 58 having an adaptor sleeve 58a threaded to heating capsule 48 adjacent end 48d and adapted to receive nose portion 58c by means of threads 58b formed with adaptor sleeve 58a engaging compatible threads (not shown) formed with nose portion 58c. As shown in FIG. 8, the blade 60j has been inserted and is appropriately locked in position in collet 58 by appropriate rotation of the nose portion 58c with respect to the adaptor sleeve 58a thus frictionally engaging and locking such blade 60j therewith.

Figure 2:
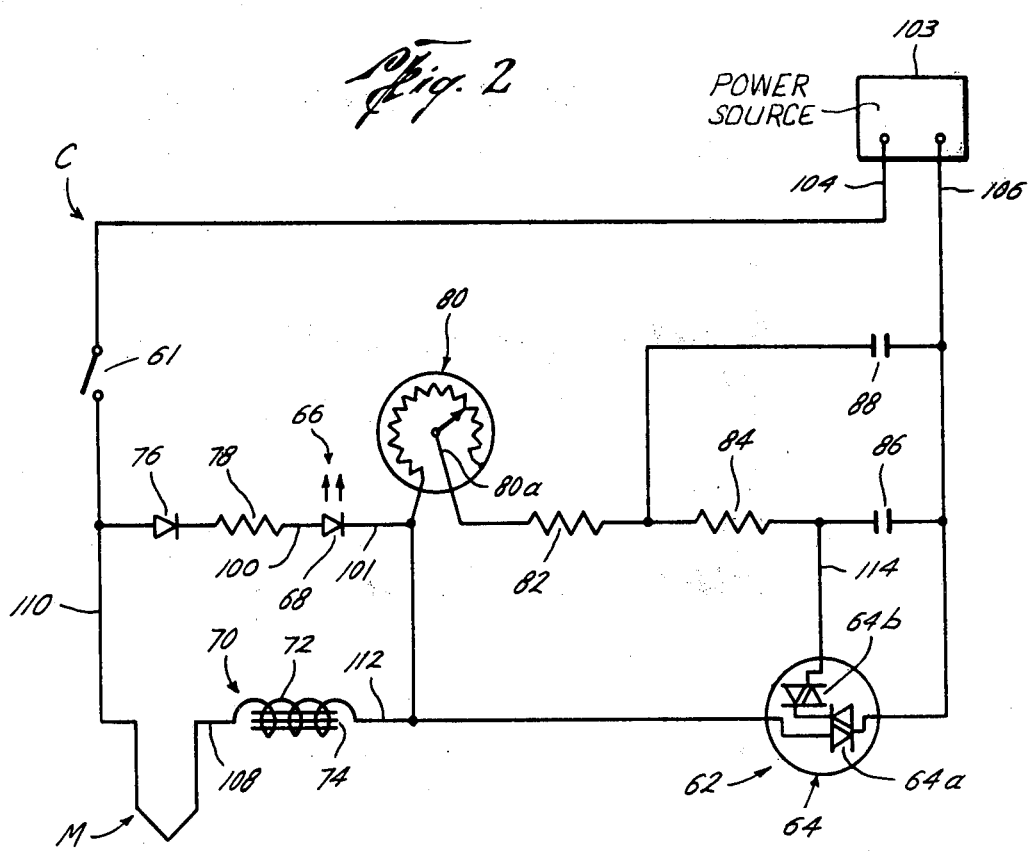
FIG. 2 is a schematic electric circuit diagram of the electronic control circuit for the heating device of the present invention.

The heating device D of the present invention further includes an electronic control circuit for selectively controlling a heating temperature of the heating means M over various selected heating ranges. As shown in FIG. 2, the electronic control circuit C includes an on-off switch 61 and a gating means 62 for limiting the interval of current flow to the heating means M for controlling the heating temperature of the heating means M. Preferably, the gating means 62 includes a voltage responsive electronic switch 64 such as that marketed under the trademark "QUADRAC" manufactured by Electronics Control Corporation which is a self-contained, solid state electronic switching device consisting of a triac 64a and an internally circuited trigger diac 64b which triggers triac 64a to permit current flow therethrough.

The electronic control circuit C further includes indicating means 66 in parallel with heating means M for indicating current flow in the heating means M and varying in intensity proportionally to the heat generated in the heating means M over various selected heating ranges. The indicating means 66 may include a light emitting diode 68 which will vary in light intensity according to the current flowing into and thus heat generated in said heating means M. Diode 76 protects the light emitting diode 68 from reverse electric current flow while resistor 78 limits the amount of forward current flowing through the diode 76.

The electronic control circuit C further includes choke means 70 in series with the heating means M to reduce electromagnetic interference caused by electromagnetic radiation from the heating means M. Preferably, the choke means 70 includes coil 72 preferably having a ferrite core 74 whose high inductive reactance impedance reduces or chokes out such high-frequency radiation.

The electronic control circuit C further includes a variable potentiometer 80 for selectively controlling, in a manner to be set forth, current flow to the heating means M over a variety of heating temperatures. Resistors 82, 84 and capacitors 86, 88 serve as an R-C filter to dampen surging and have impedance values chosen to control the operating range of the switch 64 so that heating means M provides the desired variable temperature control for a given temperature range by appropriate adjustment of the variable potentiometer 80 over the selected temperature range.

Printed circuit board 90 (FIG. 3) is adapted to be disposed within the cavity 20 formed in the enlarged housing portion H of the body member B. The printed circuit board 90 is preferably of a rectangular configuration having notched corners to correspond to notches 91 formed in cavity 20 for locating printed circuit board 90 therein the cavity 20. The variable potentiometer 80, resistors 78, 82, 84, capacitors 86, 88, diode 76 and switch 64 are preferably mounted on printed circuit board 90. Potentiometer 80 includes a shaft 80a which extends through an opening 18c formed in the top portion 18 having a bushing 92 mounted therebetween the shaft 80a and opening 18c to seal cavity 20 from the external environment adjacent thereto. The switch 61 may be mounted with potentiometer 80 adjacent the lower portion thereof and operably connected thereto by shaft 80a extending through such potentiometer 80 to engage and operate switch 61 by rotation of shaft 80a. A knob 94 is affixed to the shaft 80a to facilitate rotation thereof in adjusting the variable potentiometer 80. Preferably, the knob 94 has a full 360° scale of graduations which are numbered and correspond to temperatures achievable by the heating device D over the full temperature range desired. Preferably, the knob 94 has a zero mark (not shown) which corresponds to the "off" mode of the heating device D. Rotation of the knob 94 results in variation of current flowing in the heating means M as described more fully below.

The knob 94 fits within and conforms to a recess 96 formed in the top portion 18. The light emitting diode 68 is preferably mounted with the top portion 14 adjacent the knob 94 by means of a suitable mounting connection 98 for sealing cavity 20 from the surrounding environment. Leads 100, 101 (FIGS. 2, 3) connect the light emitting diode 68 with the components mounted with the printed circuit board 90. The sealed cavity 20 should have sufficient "dead" space to accommodate a normal temperature rise of 55° centigrade continuously without hampering or adversely affecting the function of any or all components of the electronic control circuit C.

A socket 102 (FIG. 3) is preferably mounted with the rear portion 17 of the body member B within opening 17a formed therewith. The socket 102 may be of a male and/or female configuration and shielded in such a manner that little or no possibility of shorting or shocking the user of the heating device D of the present invention will result. For example, male prongs 102a (FIG. 3) are adapted to be received by the female socket 102b such that little, if any, potential for electrical shorting or failure is manifest. Leads 104, 106 connect the socket 102 with the electronic control circuit C.

An electrical power source 103 for the heating device D of the present invention may include alternating current, direct current, or any other suitable electrical powering source and may be connected with the heating device D by an appropriate cable 103a. When the power source 103 is a direct current or other suitable electrical power source, it is appreciated that some appropriate means, such as an invertor in the case of direct current, must be provided to convert the direct current to an alternating current of proper frequency. Further, it should be noted that when operating under alternating current, the electronic control circuit C is designed for full-wave heating operation as will be discussed more fully hereinbelow. Where direct current is used as the electrical power, the socket 102 should be arranged so that the polarity of the power supply coincides to the polarity of the electronic control circuit C.

The choke means 70 is preferably mounted within the bore 24f (FIG. 3) formed in neck 24, adjacent the socket 50 and connected thereto by lead 108. Lead 110 (FIGS. 2 and 3) connects the socket with the power source 103 while lead 112 connects the choke means 70 with the remaining circuit components in accordance with the schematic of FIG. 2. Preferably, an insulating material 114 such as Dow-Corning silicone encapsulating or potting compound is used to mount, surround, seal, insulate and locate the choke 70 in the bore 24f of the neck 24. By doing so, a reduction in the overall size of the cavity 20 is accomplished while further protecting and effectively isolating the heat-sensitive electronic components of the electronic control circuit C from the heat generating heating means M.

Considering again the control circuit C, the resistances of potentiometer 80 and resistors 82, 84 of the electronic control circuit C should have impedance values chosen to give optimum control of the heating means M over a selected temperature range, as will be set forth below. The capacitors 86, 88 are utilized for fine, temperature control and act as a balance to prevent pulsating of an alternating current power source. More specifically, capacitor 88 provides for discrete control at lower temperatures while capacitor 86, as the capacitance increases, results in more temperature control at the higher temperatures generated by the heating means M.

The operation of the electronic control circuit C of the heating device D of the present invention is schematically shown in FIG. 6 which represents the waveform of heating current drawn by the heating means M. The heat that is generated by the heating capsule, such as heating capsule 44, is directly related to the duration of current flow within the heating element 44c. As noted hereinabove, the switch 64 is a self-contained solid state electronic switch having a triac 64a and an internally circuited trigger diac 64b and acts a voltage responsive electronic switch. As such, a certain required triggering voltage is required to be present for the diac 64b to activate the triac 64a. The time necessary for charging capacitors 86 and 88 to achieve such a triggering voltage is determined by current flowing thereto and is dependent on the impedance of resistors 80, 82 and 84 and consequently, is variable and proportional to the changes in the impedance caused by adjusting the potentiometer 80 with knob 94. For example, by choosing resistor 78 at 3.5 K ohms, resistor 82 at 10 K ohms, resistor 84 at 56 K ohms, capacitor 86 at 0.020 microfarads, capacitor 88 at 0.018 microfarads and by choosing a switch 64 requiring a gating current of 50 milliamps, a balanced, controlled temperature range from 0°-1000° F. at the heating means M is obtained.

As noted above, a variation in resistance of the potentiometer 80 results in a change in the impedance of the portion of electronic control circuit C controlling the switch 64. The charge rate of the capacitors 86, 88 determines the interval of time necessary for such capacitors 86, 88 to reach their required voltages. While charge is accumulating in capacitors 86, 88, no current flows through the heating means M. However, once the capacitors 86, 88 are fully charged to the triggering voltage, the diac 64b of the switch 64 causes the triac 64a to conduct, allowing current to flow therethrough the heating means M. Once current flow is established therethrough the heating means M, the light emitting diode 68, being connected in parallel to the heating means M, signifies such current flow by illuminating. As current flow increases in the heating means M, a similar response is recorded by the light emitting diode 68, resulting in greater light intensity. Thus, an increase in current flowing through the heating means M results in greater light intensity being emitted by the light emitting diode 68 resulting in a visible variable indicator of the variable amounts of heat capable of being generated by the heating means M.

High impedance, i.e. high resistance in potentiometer 80, results in low current flow within the circuitry. Inasmuch as the switch 64 requires 50 milliamps for proper gating, until such value is reached, there is no current flow through the heating means M. Thus, high resistances result in extended intervals of time necessary to charge the capacitors 86, 88 to result in gating of the switch 64 whereas lowering the resistance of the potentiometer 80, hence the circuit impedance, reduces the time interval necessary to charge the capacitors 86, 88 to sufficient level to allow gating of the switch 64 to result in current flow through the heating means M. As resistance is lowered, the time for switching the switch 64, which limits the duration of current flow, is reduced. As shown in FIG. 6, assuming a constant voltage alternating current input, $t_0$ signifies the minimum current required to charge the capacitors 86, 88 for proper gating of the switch 64. At resistances higher than this corresponding current amount, the switch 64 will not gate, consequently no heating is obtained. However, once the resistance is reduced, the time interval for charging is reduced increasing current flow sufficient to allow gating of the switch 64 as may be signified by time period $t_1$. Inasmuch as the total current is represented by the area under the current waveform 120, a further reduction in impedance will result in an increased current flow through the heating means M while shortening the time interval to that designated by $t_3$. Conversely, increasing the impedance results in an increased time interval $t_2$ which lowers the total current through the heating means M. Thus, the potentiometer 80 in conjunction with the switch 64 effectively controls the interval of time that current may be drawn by the heating means M once the minimum, gating current, such as the 50 milliamps, has been reached. Should the current be insufficient for gating of the switch 64, no heating results and the heating device D of the present invention is in its "off" mode. Reducing the impedance to the point where gating occurs results in limited current flow through the heating means M, hence lower temperatures while decreased impedance increases the interval wherein current may flow through the heating means M, resulting in higher temperatures, noting that at all times the light emitting diode 68 acts as a visual indicator of the relative temperature adjacent the blades or tips 60 of the heating means M. Diode 68 gates on and off during each cycle of the current waveform 120, but this flicker is imperceptible to the human eye.

The heating device D of the present invention is designed for working waxes used in investment casting by the "lost-wax process," such process being used in dental, jewelry, precision instrument, and other professional and industrial trades. The heating device D outfitted with proper blades 60 may be used for delicate light soldering jobs that use various types of soft solder and furthermore has use in various surgical cauterization procedures with special blades 60. The heating device D is heat, water, oil, aromatic gas-proof and is formed of a tough, easily molded plastic of high durability. Further, the heat sensitive electronic components are effectively isolated from the heating means M to prevent unwanted deterioration thereof.

The adaptability of the heating device D of the present invention to accommodate heating capsules 44, 46, 48 of varying lengths, allows the heating device D to be held by various people having various sized hands in a comfortable position, similar to holding a fountain pen. Few people have the same grip and/or manner for holding or gripping such a device. Heating capsules 44, 46, 48 and sleeves 32, 36, 40 of varying lengths allow the heating device D of the present invention to be modified such that the heating device D may be comfortably held in the hand.

Furthermore, the enlarged housing portion H of the body member B is external of the user's hand from the remainder of the device D and acts as a counterbalance to the neck portion N, sleeve means S and heating means M for balanced, operating ease by the user. This allows the user ease in controlling the heating device D without the need for undue gripping pressure. Further, the balanced configuration promotes ease of user's use in those situations where high tip pressures are necessary. The interchangeability feature of various length heating capsules allows the same basic heating device D to be used with only replacement of such heating capsules as are necessary to accommodate large varieties and sizes of hands and mannerisms necessary for holding and use. The balance of the heating device D in the hand is an important feature of the present invention as well as having full hand-held temperature control for the necessary heat capabilities to perform the necessary work. Further, the user may adjust the temperature with one hand while holding the heating means M against a workpiece with the other hand.

Thus, the heating device D of the present invention provides a new and improved hand-held, variable temperature controlled, environmental proof, solid state, thermally insulated heating device capable of providing localized heating over various selected heating ranges for a wide variety of applications.

The foregoing disclosure and description of the invention are illustrative and explanatory thereof, and various changes in the size, shape and materials as well as in the details of the illustrated construction and circuitry may be made without departing from the spirit of the invention.

I claim:

1. An electrically powered heating device adapted to be held in the hand of a user, comprising:
    elongated electrical heating means for providing localized heating over various selected heating ranges for a variety of applications, said elongated electrical heating means comprising;
    an elongated substantially rigid tubular sheath;
    an electric heating element in said sheath;
    terminal means at one end of said sheath; and,
    collet means at the other end of said sheath for removably receiving and holding a heating tip in a heat exchange relation to said electric heating element;
    an elongated sleeve means of thermally insulative material disposed in spaced relation about and covering a major portion of said heating means for gripping by the user and for thermally insulating the user's hand from said heating means, said collet means being spaced from one end of said sleeve means;

a body member formed having an enlarged housing portion and a reduced neck portion, said neck portion releasably engaging said terminal means of said heating means, said neck portion having a first end and a second end, said first end formed with said enlarged housing portion providing a thermal barrier between said heating means and said enlarged housing portion, said second end adapted to releasably engage the other end of said sleeve means;

an electronic control circuit coupled to said heating means for selectively controlling a heating temperature of said heating means over various selected heating ranges; and said enlarged housing portion formed with a cavity therein for housing said electronic control circuit.

2. The heating device of claim 1, wherein:

said terminal means of said heating means is threadedly mounted with said neck portion of said body member such that said terminal means may be positively connected with and easily removed from said body member for various heating applications.

3. The heating device of claim 1, wherein:

said sleeve means is threadedly affixed with said neck portion to enhance the removability of said sleeve means for accommodating various sleeve means of differing insulating capacities for the various selected heating ranges of said heating means.

4. The heating device of claim 3, wherein said sleeve means further includes:

an insulating bushing formed with said sleeve means and adapted to be disposed about said heating means within said sleeve means for insulating the areas adjacent the gripping by user's hand from the heat generated by said heating means.

5. The heating device of claim 4, wherein:

said insulating bushing is formed of a synthetic resin polymer.

6. The heating device of claim 3, wherein said sleeve means further includes:

ventilation means formed with said sleeve means for allowing air flow about said sleeve means for promoting the cooling of areas adjacent to the user's grip allowing for comfortable and extended use.

7. The heating device of claim 1, wherein said electronic control circuit includes:

gating means for limiting the interval of current flow to said heating means for controlling said heating temperature for said heating means.

8. The heating device of claim 7, wherein:

said gating means includes a voltage responsive electronic switch.

9. The heating device of claim 1, further including:

indicating means mounted with said body member for indicating current flow in said heating means, said indicating means varying in light intensity proportionally to the heat generated in said heating means over various selected heating ranges.

10. The heating device of claim 9, wherein:

said indicating means is a light emitting diode.

11. The heating device of claim 1, further including:

choke means connected in said electronic control circuit to reduce electromagnetic interference caused by electromagnetic radiation from said heating means.

12. The heating device of claim 1, wherein said electronic control circuit includes:

a variable potentiometer for selectively controlling current flow to said heating means over a variety of heating temperatures.

13. The heating device of claim 1, wherein:

said enlarged housing portion of said body member counterbalances said neck portion, said sleeve means, and said heating means for balanced, operating ease by the user.

14. The heating device of claim 1, wherein:

said first end of said neck portion conforms substantially to the contour of the portion of the user's hand between the thumb and forefinger providing a heating device rest for said body member on the user's hand, to enhance the user gripping said sleeve means with the fingers of the user's hand.

* * * * *